US011786120B2

United States Patent
Glik et al.

(10) Patent No.: US 11,786,120 B2
(45) Date of Patent: *Oct. 17, 2023

(54) DYNAMIC EYE FIXATION FOR RETINAL IMAGING

(71) Applicant: Verily Life Sciences LLC, South San Francisco, CA (US)

(72) Inventors: Eliezer Glik, San Francisco, CA (US); Sam Kavusi, Menlo Park, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/839,951

(22) Filed: Jun. 14, 2022

(65) Prior Publication Data
US 2022/0322934 A1    Oct. 13, 2022

Related U.S. Application Data

(63) Continuation of application No. 16/584,606, filed on Sep. 26, 2019, now Pat. No. 11,389,060.
(Continued)

(51) Int. Cl.
*A61B 3/12*    (2006.01)
*A61B 3/14*    (2006.01)
(Continued)

(52) U.S. Cl.
CPC ............. *A61B 3/12* (2013.01); *A61B 3/0091* (2013.01); *A61B 3/14* (2013.01); *G06T 7/0016* (2013.01);
(Continued)

(58) Field of Classification Search
CPC .......... A61B 3/12; A61B 3/0091; A61B 3/14; A61B 3/152; A61B 3/0025; G06T 7/0016;
(Continued)

(56) References Cited

U.S. PATENT DOCUMENTS 5,585,873 A    12/1996    Shalon et al.
6,637,882 B1   10/2003    Goldfain et al.
(Continued)

FOREIGN PATENT DOCUMENTS

JP    2012223428 A    11/2012
JP    2013537092 A     9/2013
(Continued)

OTHER PUBLICATIONS

Japanese Decision of Rejection, dated Sep. 28, 2022, in corresponding Japanese Patent Application No. 2021-518917, 4 pages.
(Continued)

*Primary Examiner* — Mohammed A Hasan
(74) *Attorney, Agent, or Firm* — CHRISTENSEN O'CONNOR JOHNSON KINDNESS PLLC

(57) ABSTRACT

A retinal imaging system includes an eyepiece lens assembly, an image sensor, a dynamic fixation target viewable through the eyepiece lens assembly, and a controller coupled to the image sensor and the dynamic fixation target. The controller includes logic that causes the retinal imaging system to perform operations including: acquiring a first image of the eye, analyzing the first image to determine whether a misalignment between the eye and the eyepiece lens assembly is present; in response to determining the misalignment is present, adjusting a visual position of the dynamic fixation target to encourage the eye to rotate in a direction that compensates for the misalignment, and acquiring the retinal image of the eye after adjusting the visual position of the dynamic fixation target.

20 Claims, 9 Drawing Sheets

Related U.S. Application Data

(60) Provisional application No. 62/753,570, filed on Oct. 31, 2018.

(51) Int. Cl.
*A61B 3/00* (2006.01)
*G06T 7/73* (2017.01)
*G06T 7/20* (2017.01)
*G06T 7/00* (2017.01)

(52) U.S. Cl.
CPC .................. *G06T 7/20* (2013.01); *G06T 7/74* (2017.01); *G06T 2207/10048* (2013.01); *G06T 2207/30041* (2013.01)

(58) Field of Classification Search
CPC ... G06T 7/20; G06T 7/74; G06T 2207/10048; G06T 2207/30041; G06T 7/73
USPC ....................................................... 351/208
See application file for complete search history.

(56) References Cited

U.S. PATENT DOCUMENTS

| | | | |
|---|---|---|---|
| 7,524,062 | B2 | 4/2009 | Iwa et al. |
| 7,677,730 | B2 | 3/2010 | Shimizu |
| 8,421,855 | B2 | 4/2013 | Buckland et al. |
| 8,708,490 | B2 | 4/2014 | Baranton et al. |
| 9,039,176 | B2 | 5/2015 | Honda et al. |
| 9,254,084 | B2 | 2/2016 | Yoshino et al. |
| 9,370,303 | B2 | 6/2016 | Tanaka et al. |
| 9,498,126 | B2 | 11/2016 | Wang |
| 9,532,708 | B2 | 1/2017 | Juhasz et al. |
| 9,743,832 | B2 | 8/2017 | de Paz Sicam et al. |
| 9,918,629 | B2 | 3/2018 | Wang |
| 11,389,060 | B2 * | 7/2022 | Glik .......................... G06T 7/73 |
| 2008/0002152 | A1 | 1/2008 | Collins et al. |
| 2013/0181976 | A1 | 7/2013 | Dastmalchi et al. |
| 2013/0194548 | A1 | 8/2013 | Francis et al. |
| 2016/0338589 | A1 * | 11/2016 | Carrasco-Zevallos ....................... A61B 3/113 |
| 2017/0100032 | A1 | 4/2017 | Zakariaie et al. |
| 2017/0164830 | A1 | 6/2017 | Huang et al. |
| 2018/0008460 | A1 | 1/2018 | Tanzer |
| 2019/0046031 | A1 * | 2/2019 | Kramer ................ A61B 3/0008 |
| 2019/0110677 | A1 | 4/2019 | Walsh et al. |
| 2019/0125184 | A1 | 5/2019 | Kramer et al. |
| 2019/0199893 | A1 * | 6/2019 | Kramer .................. H04N 23/51 |
| 2020/0305711 | A1 | 10/2020 | Kramer |

FOREIGN PATENT DOCUMENTS

| | | |
|---|---|---|
| JP | 2016510628 A | 4/2016 |
| JP | 2019170468 A | 10/2019 |
| WO | 2010009447 A3 | 1/2010 |
| WO | 2014158263 A | 10/2014 |
| WO | 2015054672 A1 | 4/2015 |

OTHER PUBLICATIONS

Extended European Search Report, dated Jun. 22, 2022, in corresponding European Patent Application No. 19879919.9-1126, 7 pages.
International Search Report and Written Opinion dated Jun. 9, 2020 in corresponding International Patent Application No. PCT/US2020/024193, 9 pages.
Welch Allyn RetinaVue 100 Imager, Directions for Use, 2018, pp. 1-116.
DualAlign 12K Retina, Registering and Aligning Fundus Images, 2010, TopCon Medical Systems, Inc.
Muqit et al., Optos-guided pattern scan laser (Pascal)-targeted retinal photocoagulation in proliferative diabetic retinopathy, Acta Opthalmolgica, Dec. 2011, pp. 251-259.
Klein et al., Megahertz OCT for ultrawide-field retinal imaging with a 1050nm Fourier domain mode-locked laser, Optics Express vol. 19, No. 4, Feb. 14, 2011, pp. 1-19.
DeHoog et al., Optimal Parameters for retinal illumination and imaging in fundus cameras, Applied Optics, vol. 47, No. 36, Dec. 20, 2008, pp. 6769-6777.
Retinal Camera TRC-50X, TopCon, Instruction Manual.
TopCon Introduces the TRC-NW400 Non-mydriatic Retinal Camera with Fully Automatic Functions for Alignment, Focusing and Capturing Color Retinal Images, OpthamologyWeb, Sep. 10, 2018.
Retinal Camera TRC-50DX, TopCon, Instruction Manual, pp. 1-80.
TRC-NWSF Mark II, TopCon, Brochure pp. 1-4.
International Search Report and Written Opinion dated Jan. 30, 2020 in corresponding International Patent Application No. PCT/US2019/057647, 8 pages.
Australian Examination Report, dated Oct. 1, 2021, in corresponding Australian Patent Application No. 2019371199, 5 pages.
Canadian Examination Report, dated May 31, 2022, in corresponding Canadian Patent Application No. 3116741, 3 pages.
Japanese Office Action, dated May 31, 2022, in corresponding Japanese Patent Application No. 2021-518917, 5 pages.

* cited by examiner 0 mm Y SHIFT 1.5 mm Y SHIFT

DYNAMIC EYE FIXATION FOR RETINAL IMAGING

CROSS-REFERENCE TO RELATED APPLICATIONS

This application is a continuation of U.S. application Ser. No. 16/584,606, filed Sep. 26, 2019, which claims the benefit of U.S. Provisional Application No. 62/753,570, filed on Oct. 31, 2018, the contents both of which are incorporated herein by reference.

TECHNICAL FIELD

This disclosure relates generally to retinal imaging technologies, and in particular but not exclusively, relates to fixation targets for retinal imaging.

BACKGROUND INFORMATION

Retinal imaging is a part of basic eye exams for screening, field diagnosis, and progress monitoring of many retinal diseases. A high fidelity retinal image is important for accurate screening, diagnosis, and monitoring. Bright illumination of the posterior interior surface of the eye (i.e., retina) through the pupil improves image fidelity but often creates optical aberrations or image artifacts, such as corneal reflections, iris reflections, or lens flare, if the retinal camera and illumination source are not adequately aligned with the eye. Simply increasing the brightness of the illumination does not overcome these problems, but rather makes the optical artifacts more pronounced, which undermines the goal of improving image fidelity.

Accordingly, camera alignment is very important, particularly with conventional retinal cameras, which typically have a very limited eyebox due to the need to block the deleterious image artifacts listed above. The eyebox for a retinal camera is a three dimensional region in space typically defined relative to an eyepiece of the retinal camera and within which the center of a pupil or cornea of the eye should reside to acquire an acceptable image of the retina. The small size of conventional eyeboxes makes retinal camera alignment difficult and patient interactions during the alignment process often strained.

Various solutions have been proposed to alleviate the alignment problem. For example, moving/motorized stages that automatically adjust the retina-camera alignment have been proposed. However, these stages tend to be mechanically complex and substantially drive up the cost of a retinal imaging platform. An effective and low cost solution for efficiently and easily achieving eyebox alignment of a retinal camera would improve the operation of retinal cameras.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of an apparatus, system, and method of operation for dynamically adjusting a fixation target of a retinal camera system to encourage a compensating eye roll maneuver that offsets lateral misalignment between the retinal camera system and an eye are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
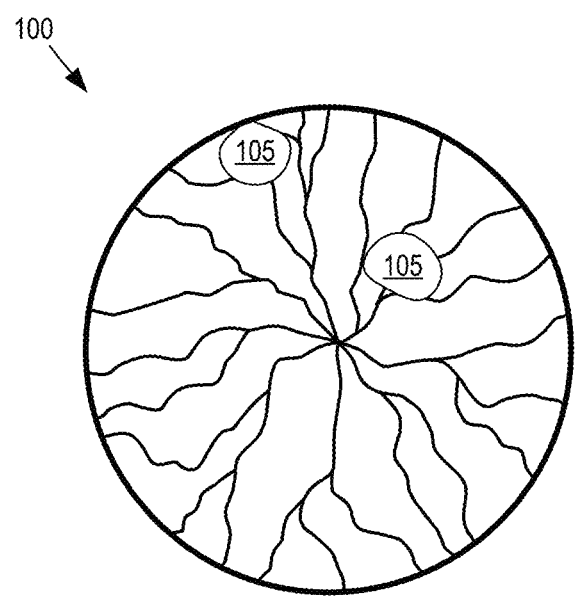
FIG. 1 illustrates a retinal image including an demonstrative image artifact due to misalignment of the retinal camera.

High fidelity retinal images are important for screening, diagnosing, and monitoring many retinal diseases. To this end, reducing or eliminating instances of image artifacts that occlude, or otherwise malign portions of the retinal image is desirable. FIG. 1 illustrates an example retinal image 100 with multiple image artifacts 105. These image artifacts may arise when misalignment between the retinal imaging system and the eye permit stray light and deleterious reflections from the illumination source to enter the imaging path and ultimately are captured by the image sensor with the retinal image light. Misalignment can lead to deleterious corneal/iris reflections, refractive scattering from the crystalline lens, occlusion of the imaging aperture, optical aberrations due to off axis passage through the crystalline lens, the blockage of imaging light by the iris, and/or other issues.

Conventional imaging systems have relatively small eyeboxes, which require precise alignment to avoid image artifacts from entering the image path. Embodiments described herein utilize a dynamic fixation target not just as a static point to stabilize a patient's fixation, select the center ray of the patient's field of view (FOV), and lock the patient accommodation at a fixed depth, but also to aid in the alignment and retinal image optimization. In particular, embodiments described herein incorporate a dynamic fixation target that moves in real-time based upon retinal image quality and/or eye tracking to encourage the patient's eye to roll in a direction that compensates for a lateral misalignment (decentering) between the eyepiece of the retinal imaging system and the patient's eye. The dynamic adjustment of the fixation target expands the eyebox without the use of complicated or costly mechanical components. The expanded eyebox eases the alignment burden while reducing the instances of image artifacts/aberrations that malign the captured retinal image.

The dynamic adjustment of the fixation target may be used during a preview phase and motivated to achieve pre-retinal-imaging alignment between the user's eye and the eyepiece. The dynamic adjustments to the fixation target may also be motivated to achieve multiple alignment arrangements that move the position of an image artifact 105 between retinal images or between bursts of retinal images. It is typically desirable to move an image artifact 105 entirely out of the FOV of the image sensor when reasonably possible. However, in some instances an eye movement that achieves 100% removal of an image artifact 105 from the imaging FOV ins't readily or easily achievable. In such instances, the dynamic fixation target may be moved to encourage the patient's eye to roll in specified directions. Although the image artifact 105 may not be entirely removed from all or any of the multiple retinal images, the patient's eye is directed to roll in such a manner that each portion of the retina is clearly imaged in at least one retinal image. The multiple retinal images may then be combined or stacked to entirely remove image artifacts 105 from a composite retinal image.

Figure 2:
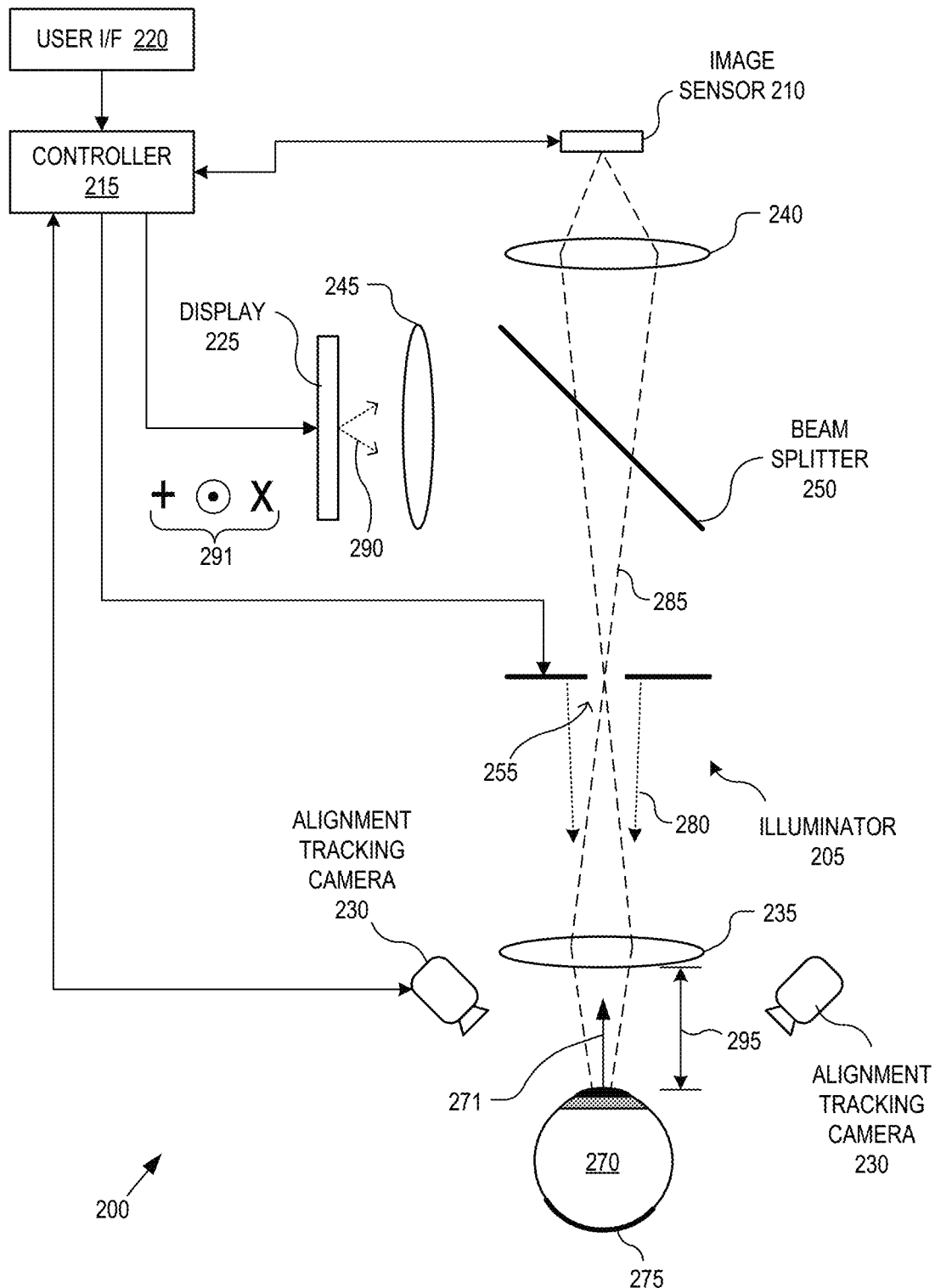
FIG. 2 illustrates a retinal imaging system with a dynamic fixation target, in accordance with an embodiment of the disclosure.

FIG. 2 illustrates a retinal imaging system 200 with a dynamic fixation target, in accordance with an embodiment of the disclosure. The illustrated embodiment of retinal imaging system 200 includes an illuminator 205, an image sensor 210 (also referred to as a retinal image sensor), a controller 215, a user interface 220, a display 225, an alignment tracking camera(s) 230, and an optical relay system. The illustrated embodiment of the optical relay system includes lens assemblies 235, 240, 245 and a beam splitter 250. The illustrated embodiment of illuminator 205 comprises a ring illuminator with a center aperture 255.

The optical relay system serves to direct (e.g., pass or reflect) illumination light 280 output from illuminator 205 along an illumination path through the pupil of eye 270 to illuminate retina 275 while also directing image light 285 of retina 275 (i.e., the retinal image) along an imaging path to image sensor 210. Image light 285 is formed by the scattered reflection of illumination light 280 off of retina 275. In the illustrated embodiment, the optical relay system further includes beam splitter 250, which passes at least a portion of image light 285 to image sensor 210 while also optically coupling dynamic fixation target 291 to eyepiece lens assembly 235 and directing display light 290 output from display 225 to eye 270. Beam splitter 250 may be implemented as a polarized beam splitter, a non-polarized beam splitter (e.g., 90% transmissive and 10% reflective, 50/50 beam splitter, etc.), a dichroic beam splitter, or otherwise. The optical relay system includes a number of lenses, such as lenses 235, 240, and 245, to focus the various light paths as needed. For example, lens 235 may include one or more lensing elements that collectively form an eyepiece lens assembly that is displaced from the cornea of eye 270 by an eye relief 295 during operation. Lens 240 may include one or more lens elements for bring image light 285 to a focus on image sensor 210. Lens 245 may include one or more lens elements for focusing display light 290. It should be appreciated that optical relay system may be implemented with a number and variety of optical elements (e.g., lenses, reflective surfaces, diffractive surfaces, etc.) and may vary from the configuration illustrated in FIG. 2.

In one embodiment, display light 290 output from display 225 represents a dynamic fixation target. The dynamic fixation target may be an image of a plus-sign, a bullseye, a cross, a target, or other shape (e.g., see demonstrative dynamic fixation target images 291). The dynamic fixation target not only can aid with obtaining alignment between retinal imaging system 200 and eye 270 by providing visual feedback to the patient, but may also give the patient a fixation target upon which the patient can accommodate and stabilize their vision. The dynamic fixation target may be moved by translating the image of the fixation target about display 225 as desired (e.g., moving the fixation target up/down or left/right on display 225). Display 225 may be implemented with a variety of technologies including an liquid crystal display (LCD), light emitting diodes (LEDs), various illuminated shapes (e.g., an illuminated cross or concentric circles), or otherwise. Of course, the dynamic fixation target may be implemented in other manners than a virtual image on a display. For example, the dynamic fixation target may be a physical object (e.g., crosshairs, etc.) that is physically manipulated.

Controller 215 is coupled to image sensor 210, display 225, illuminator 205, and alignment tracking camera 230 to choreograph their operation. Controller 215 may include software/firmware logic executing on a microcontroller, hardware logic (e.g., application specific integrated circuit, field programmable gate array, etc.), or a combination of software and hardware logic. Although FIG. 2 illustrates controller 215 as a distinct functional element, the logical functions performed by controller 215 may be decentralized across a number hardware elements. Controller 115 may further include input/output (I/O ports), communication systems, or otherwise. Controller 215 is coupled to user interface 220 to receive user input and provide user control over retinal imaging system 200. User interface 220 may include one or more buttons, dials, feedback displays, indicator lights, etc.

Image sensor 210 may be implemented using a variety of imaging technologies, such as complementary metal-oxide-semiconductor (CMOS) image sensors, charged-coupled device (CCD) image sensors, or otherwise. In one embodiment, image sensor 210 includes an onboard memory buffer or attached memory to store/buffer retinal images.

Alignment tracking camera 230 is an optional element that operates to track lateral alignment (or misalignment) between retinal imaging system 200 and eye 270, and in particular, between eyepiece lens assembly 235 and eye 270. Alignment tracking camera 230 may operate using a variety of different techniques to track the relative position of eye 270 to retinal imaging system 200 including pupil tracking, retina tracking, iris tracking, or otherwise. In the illustrated embodiment, alignment tracking camera 230 includes two cameras disposed on either side of eyepiece lens assembly 235 to enable triangulation and obtain X, Y, and Z position information about the pupil or iris. In one embodiment, alignment tracking camera 230 includes one or more infrared (IR) emitters to track eye 270 via IR light while retinal images are acquired with visible spectrum light. In such an embodiment, IR filters may be positioned within the image path to filter the IR tracking light. In some embodiments, the tracking illumination is temporally offset from image acquisition.

As discussed below in greater detail, lateral alignment may be measured via retinal images acquired by image sensor 210, or separately/additionally, by alignment tracking camera 230. In the illustrated embodiment, alignment tracking camera 230 is positioned externally to view eye 270 from outside of eyepiece lens assembly 235. In other embodiments, alignment tracking camera 230 may be optically coupled via the optical relay components to view and track eye 270 through eyepiece lens assembly 235.

During operation, controller 115 operates illuminator 205 and retinal image sensor 210 to capture one or more retinal images. Illumination light 280 is directed through the pupil of eye 270 to illuminate retina 275. The scattered reflections from retina 275 are directed back along the image path through aperture 255 to image sensor 210. When eye 270 is properly aligned within the eyebox of system 200, aperture 255 operates to block deleterious reflections and light scattering that would otherwise malign the retinal image while passing the image light itself. Prior to capturing the retinal image, controller 215 operates display 225 to output a fixation target to guide the patient's gaze. One or more initial eye images (a.k.a., initial alignment images), either from image sensor 210 or alignment tracking camera 230, are acquired and analyzed to determine the lateral alignment between eye 270 and eyepiece lens assembly 235. These initial alignment images may be illuminated with infrared (IR) light output from illuminator 205 (or an independent illuminator associated with alignment tracking camera 230) so as not to trigger an iris constriction response, which constricts the imaging path to retina 275. In other embodiments, conventional white light or other chromatic light is used to acquire the initial alignment images. The initial alignment image is then analyzed by controller 215 to identify any misalignment, reposition the dynamic fixation target to encourage an compensating eye rotation, and then acquire one or more subsequent eye images (e.g., retinal images) with image sensor 210. The subsequent images may be full color images, specific chromatic images, or even IR images as desired.

Figure 3:
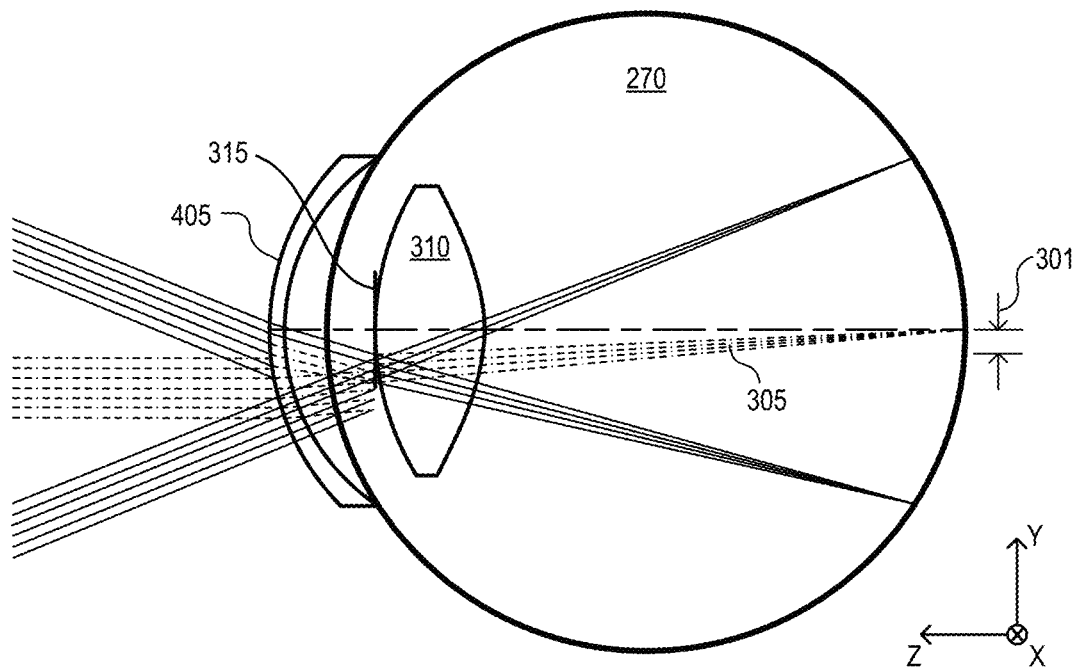
FIG. 3 is a cross-sectional diagram of an eye illustrating how a lateral offset results in reduced image quality of a retinal image.

FIG. 3 is a cross-sectional diagram of eye 270 illustrating how a lateral offset results in reduced image quality of a retinal image. When eye 270 is slightly misaligned from the ideal centered location in the X or Y direction (decenter 301), a shift of chief ray 305 occurs due to off center imaging through crystalline lens 310. FIG. 3 depicts a Y shift of 2 mm with a 4 mm diameter pupil 315. The dashed rays represent the center FOV while the solid rays represent the edge of the image plane in a 45 degree retinal image. As illustrated, pupil 315 of the iris blocks some imaging rays. The current fixation is at nominal fixation causing the user to accommodate to the target, as well as center their eye on the target. The depicted lateral offset or decentered/misalignment reduces the amount of light transmitted to the retina and creates aberrations due to the shifting of chief ray 305 and off-center imaging through crystalline lens 310 and cornea 405.

Figure 4:
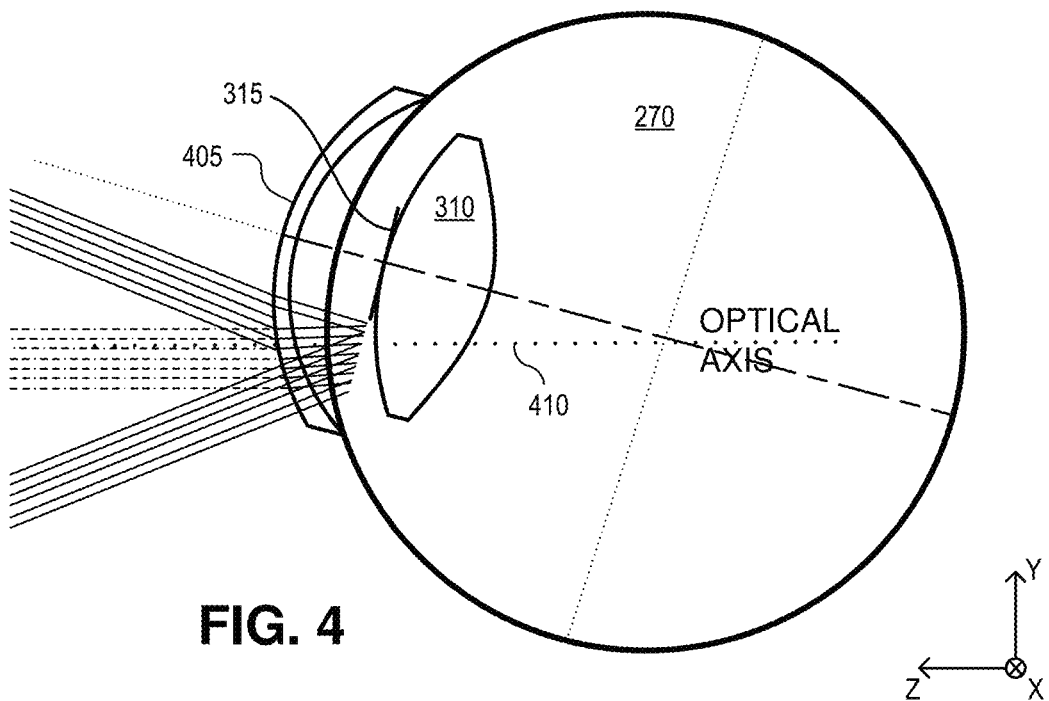
FIG. 4 is a cross-sectional diagram of an eye illustrating how rolling of an eye shifts the cornea, iris, and crystalline lens of the eye resulting in a lateral decentering from the optical axis of a retinal imaging system, in accordance with an embodiment of the disclosure.

FIG. 4 is a cross-sectional diagram of eye 270 illustrating how rotation of eye 270 shifts the cornea 405, pupil 315, and crystalline lens 310 resulting in a lateral decentering from the optical axis 410 of retinal imaging system 200. FIG. 4 depicts a 0 mm Y shift but also a 15 degree eye rotation. As illustrated, the rotation axis of eye 270 is not at cornea 405, but roughly about the center of the eyeball. This causes cornea 405, pupil 315, and crystalline lens 310 to shift forming a lateral decenter from the optical axis. While usually this is an undesired effect, this effect can also be leveraged to compensate for a lateral offset or misalignment between retinal imaging system 200 and eye 270.

Figure 5:
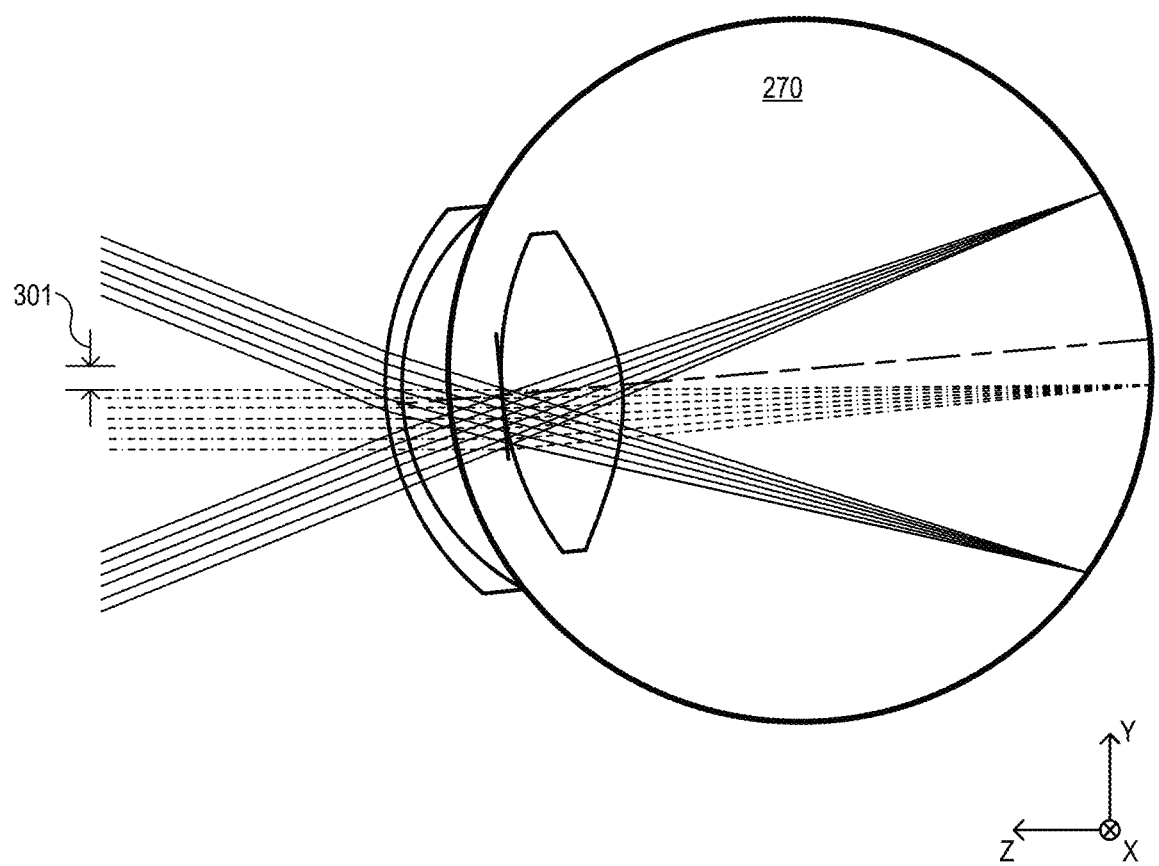
FIG. 5 is a cross-sectional diagram of an eye illustrating how a rotation of the eye can compensate for a lateral offset, in accordance with an embodiment of the disclosure.

FIG. 5 is a cross-sectional diagram of eye 270 illustrating how a rotation of eye 270 towards the direction of lateral offset 301 can compensate for the lateral offset, in accordance with an embodiment of the disclosure. FIG. 5 illustrates a 2 mm Y offset (offset 301) between eye 270 and the center optical axis through eyepiece lens assembly 235 along with a compensating 5 degrees of eye rotation towards the direction of offset. In other words, eye 270 is laterally offset 2 mm above the center of eyepiece lens assembly 235 and thus rotates down (i.e., towards the direction of the lateral offset) to compensate for the decentered misalignment.

Figure 6A:
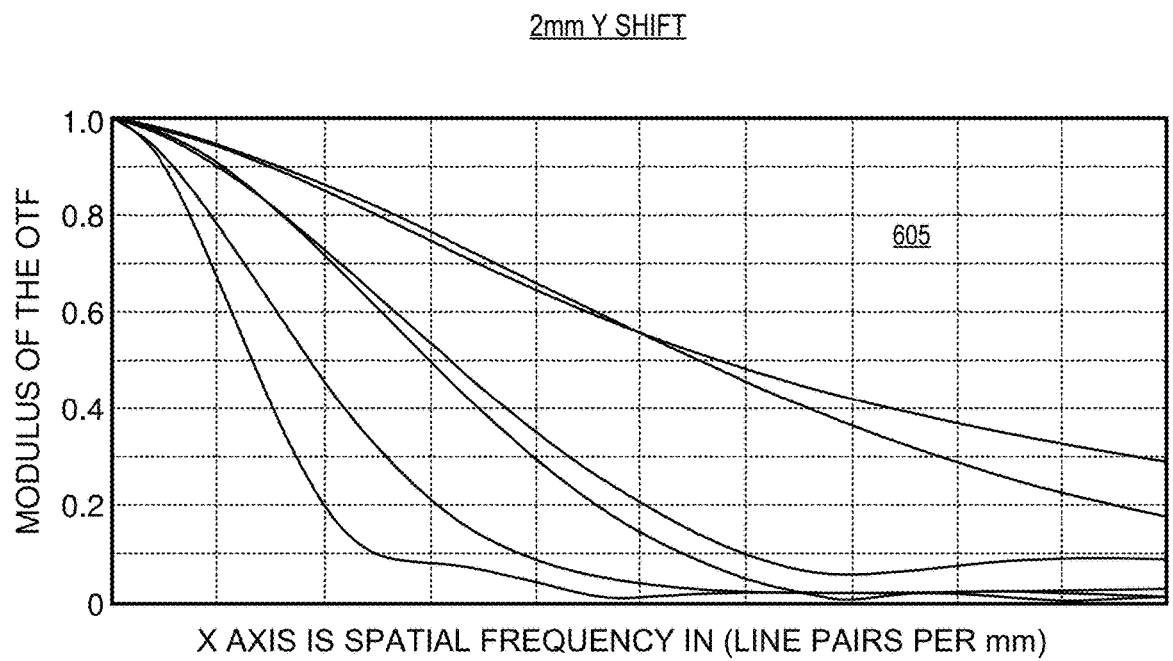
FIGS. 6A and 6B are charts illustrating how the optical transfer function for different fields of view and anatomical planes is improved by a rotation to compensate for a lateral offset, in accordance with an embodiment of the disclosure.
Figure 6B:
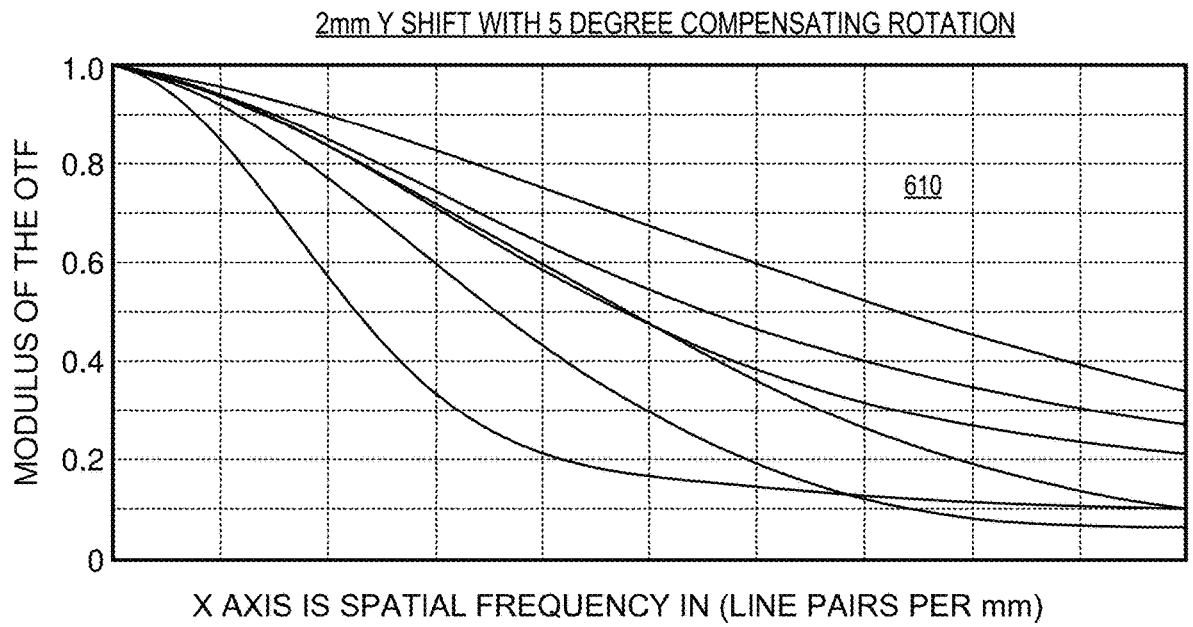

Referring to the uncompensated situation illustrated in FIG. 3, due to aberrations in cornea 405 and crystalline lens 310, the retinal image quality suffers from the lateral misalignment. However, as discussed above, the compensating rotation illustrated in FIG. 5 compensates for this loss in image quality. FIG. 6A illustrates an optical transfer function (OTF) plot 605 corresponding to the uncompensated lateral offset scenario illustrated in FIG. 3. The various lines represent OTF vs spatial frequency for different FOVs and the sagittal vs tangential planes. FIG. 6B illustrates an OTF plot 610 corresponding to the compensated lateral offset scenario illustrated in FIG. 5. As can be seen from plots 605 and 610, the 5 degree compensating rotation of eye 270 increases the OTF for all lines on plot 610, particularly the bottom lines, which represent the most off axis ray traces in the image path. The compensating rotation improves the OTF by moving the image path rays closer to the center of eye 270. Furthermore, the ray bundle size in FIG. 5 passing through pupil 315 to the retina is larger than that illustrated in FIG. 3, and therefore increases the retinal image brightness.

Figure 7:
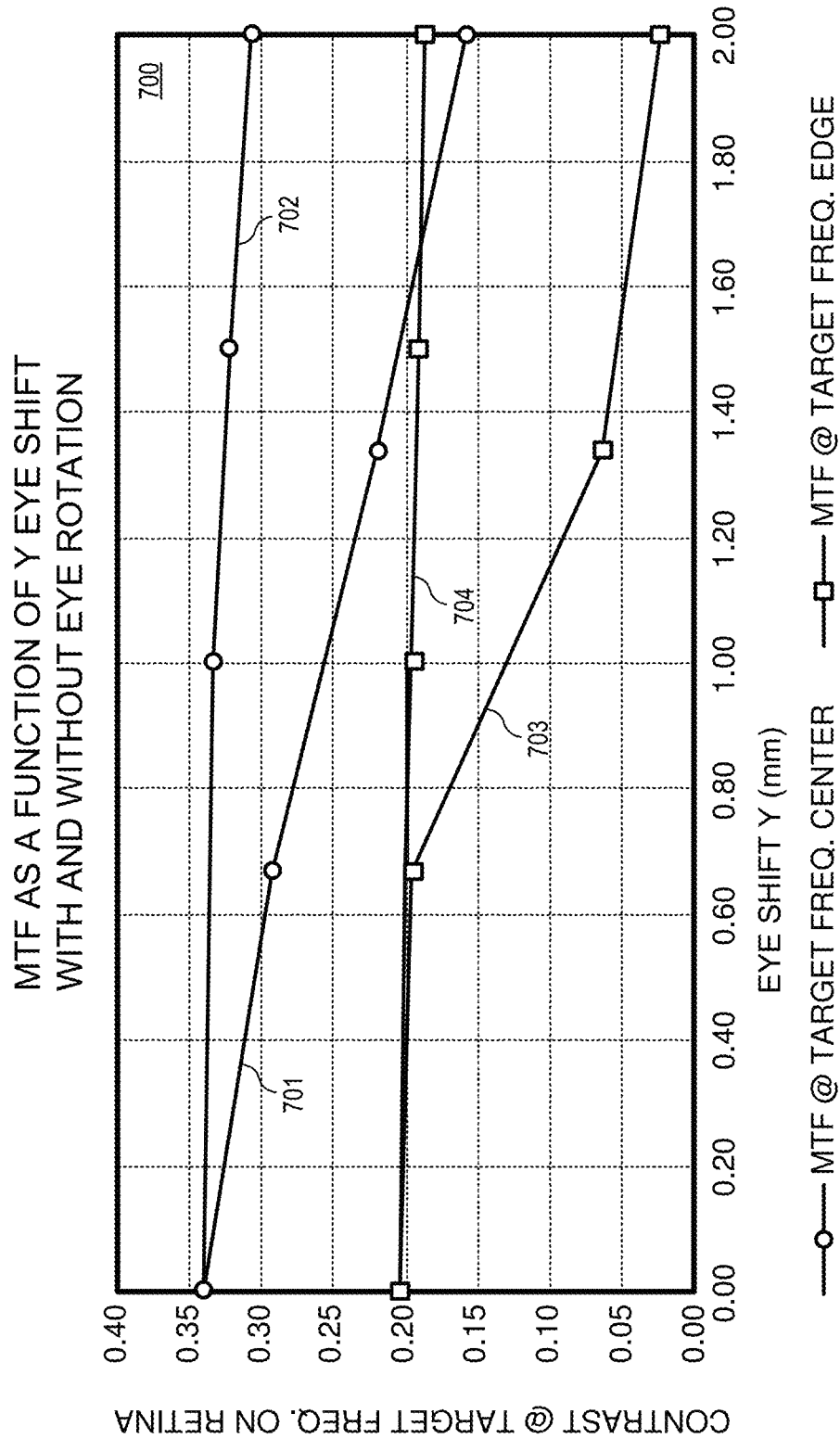
FIG. 7 is a chart illustrating how an eye rotation that compensates for a lateral offset improves image contrast along both center and edge ray traces through the imaging path, in accordance with an embodiment of the disclosure.

FIG. 7 is a chart 700 illustrating how an eye rotation that compensates for a lateral offset also improves image contrast along both center and edge ray traces through the image path, in accordance with an embodiment of the disclosure. Line 701 represents a center ray without a compensating eye roll, while line 702 represents that same center ray with a compensating eye roll. As can be seen, the compensating effect increases with greater lateral offset of eye 270 from the center of eyepiece lens assembly 235. Similarly, line 703 represents an edge FOV ray without a compensating eye roll, while line 704 represents that same edge FOV ray with a compensating eye roll. Again, the compensating effect increases with greater lateral offset of eye 270 from the center of eyepiece lens assembly 235.

Figure 8A:
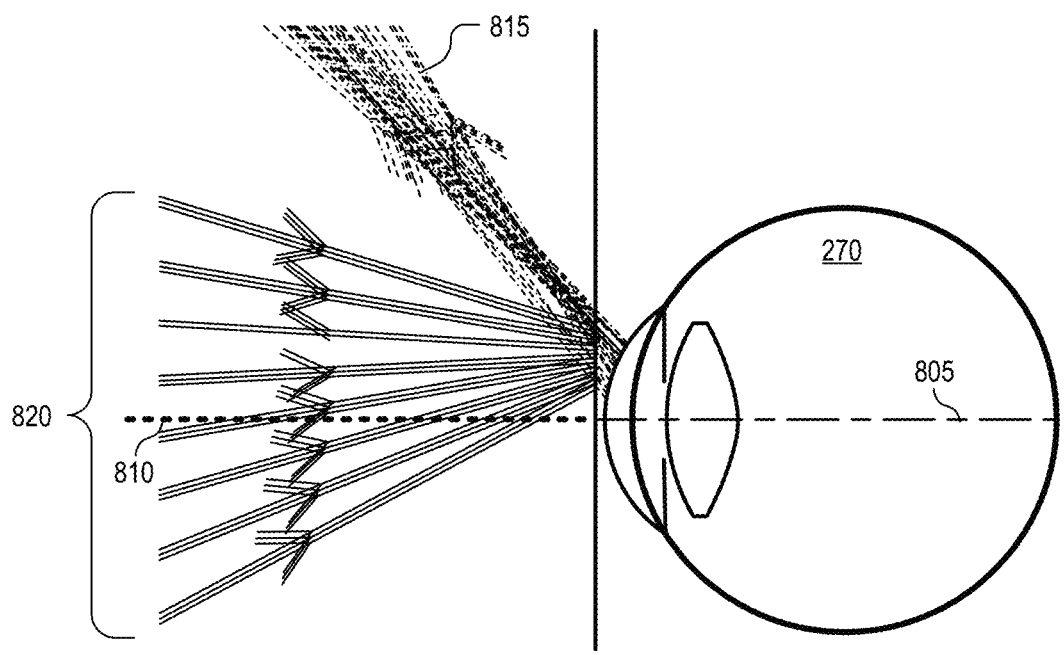
FIG. 8A is a cross-sectional diagram of an eye illustrating how a well aligned eye rejects corneal reflections from entering the imaging path, in accordance with an embodiment of the disclosure.
Figure 8B:
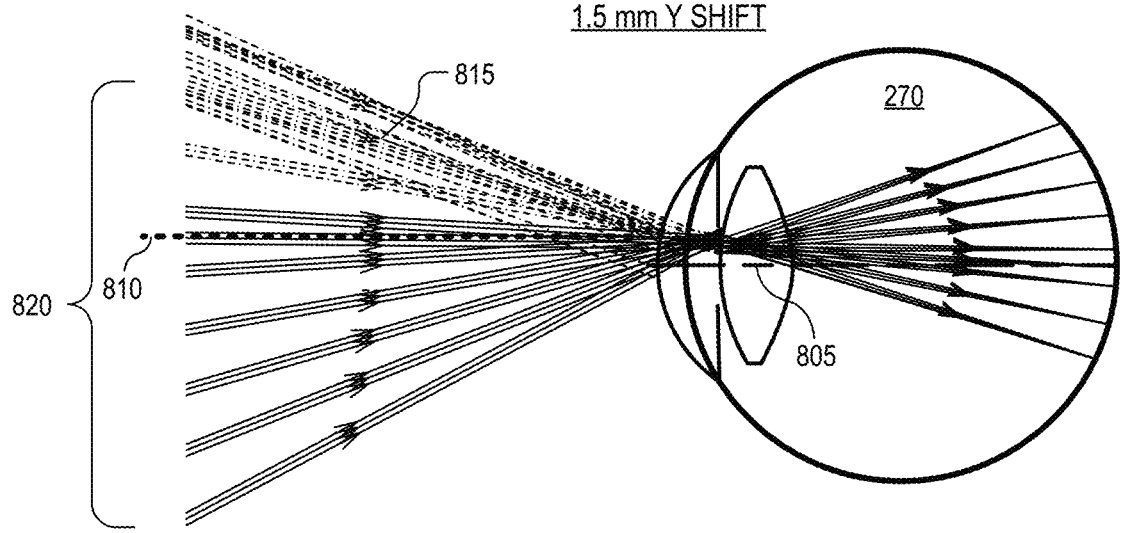
FIG. 8B is a cross-sectional diagram of an eye illustrating how a lateral offset between the eye and the retinal imaging system results in corneal reflections deleteriously entering the imaging path, in accordance with an embodiment of the disclosure.
Figure 8C:
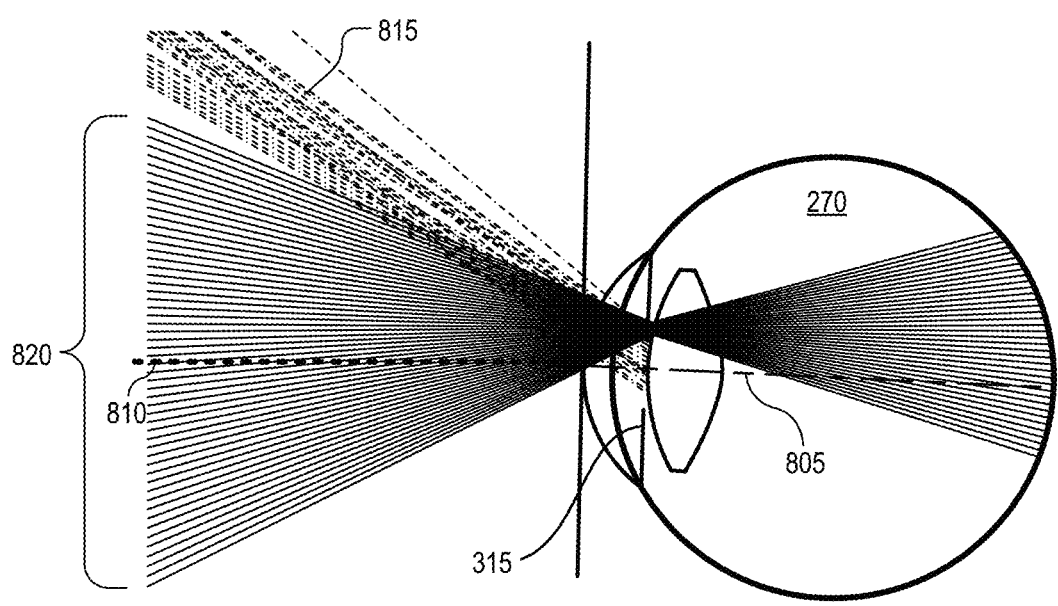
FIG. 8C is a cross-sectional diagram of an eye illustrating how an eye rotation compensates for the lateral offset resulting in corneal reflections again being rejected from entering the imaging path, in accordance with an embodiment of the disclosure.

FIGS. 8A-C illustrate how a compensatory roll of eye 270 towards the direction of a lateral offset also improves rejection of deleterious corneal reflections, in accordance with embodiments of the application. FIG. 8A illustrates an example where the center optical axis 805 of eye 270 is aligned with the center optical axis 810 of eyepiece lens assembly 235. With appropriate alignment between eye 270 and eyepiece lens assembly 235, deleterious corneal reflections 815 are separated from and directed away from imaging path 820. FIG. 8B illustrates a 1.5 mm lateral offset without any compensating eye roll. As can be seen, corneal reflections 815 enter into the imaging path 820, which malign the overall retinal image. FIG. 8C illustrates a 1.5 mm lateral offset with a compensating roll or tilt of eye 270 towards the direction of offset (in this case a tilt up). As illustrated, corneal reflections 815 are once again rejected and directed outside the imaging path 820. Additionally, a greater percentage of the incident light passes through pupil 315 of the iris to the retina resulting in a brighter retinal image.

Figure 9:
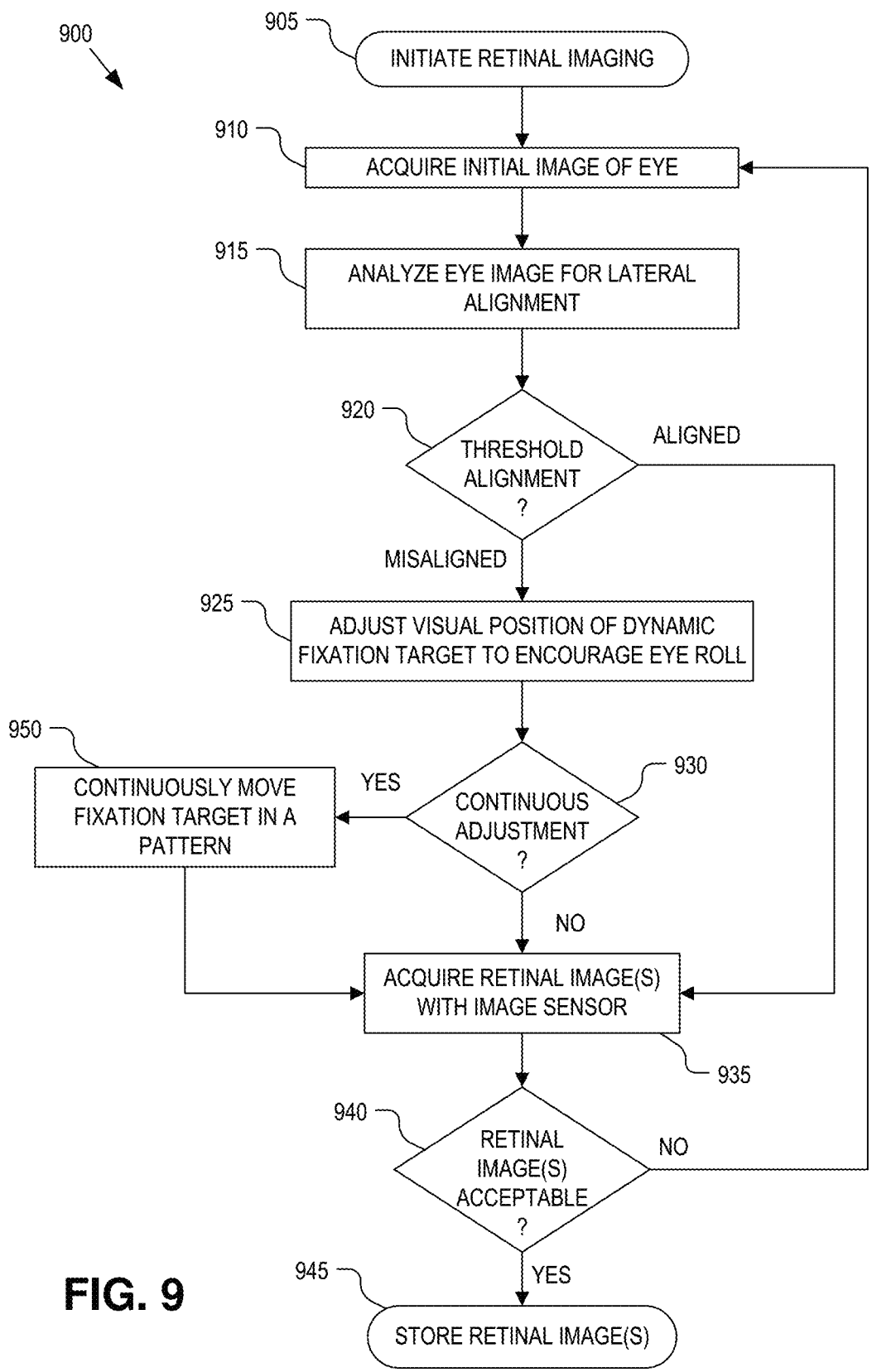
FIG. 9 is a flow chart illustrating a process of operating a retinal imaging system with a dynamic fixation target to encourage eye rotations that compensate for lateral offsets, in accordance with an embodiment of the disclosure.

FIG. 9 is a flow chart illustrating a process 900 for operation of retinal imaging system 200, in accordance with an embodiment of the disclosure. The order in which some or all of the process blocks appear in process 900 should not be deemed limiting. Rather, one of ordinary skill in the art having the benefit of the present disclosure will understand that some of the process blocks may be executed in a variety of orders not illustrated, or even in parallel.

In a process block 905, the retinal imaging process is initiated. Initiation may include the user selecting a power button from user interface 220. In a process block 910, an initial eye image is acquired with dynamic fixation target located at an initial or default position (e.g., center of display 225). The initial eye image is then analyzed by controller 215 (process block 915) to determine lateral alignment between eye 270 and eyepiece lens assembly 235. In one embodiment, the initial eye image is a retinal image acquired with image sensor 210 through eyepiece lens assembly 235. The retinal image may be analyzed to identify the characteristic presence of corneal reflections that arise due to a lateral misalignment between retinal imaging system 200 and eye 270. The presence and location of the corneal reflections in the initial retinal image can be correlated (e.g., via a lookup table) to a determined lateral offset. The corneal reflections can be correlated to both direction and magnitude of the lateral misalignment. In one embodiment, these correlations can arise due to illuminator 205 including a plurality of discrete illumination sources disposed at different radial and/or angular positions about aperture 255. Each discrete illumination source gives rise to a different characteristic reflection depending upon alignment/misalignment of system 200 with eye 270. Alternatively (or additionally), the initial retinal image may be analyzed by comparing image qualities (e.g., contrast levels, etc.) between different regions of the retinal image, and these image quality variations correlated to lateral misalignment (direction and magnitude). As described in connection with FIGS. 6A, 6B, and 7, edge FOV imaging rays are affected differently than center FOV imaging rays by lateral misalignment. This difference can be exploited and correlated to determine the direction and magnitude of a lateral misalignment between retinal imaging system 200 and eye 270.

In another embodiment, the initial eye image is captured by alignment tracking camera 230, which is a separate and distinct camera from retinal image sensor 210. Alignment tracking camera 230 images the exterior of eye 270 to perform pupil or iris tracking. Alignment tracking camera 230 may be positioned external to eyepiece lens assembly 235 to acquire the pupillary image or iris image outside of imaging path 285 (illustrated), or optically coupled into the imaging path 285 to image eye 270 through eyepiece lens assembly 235 (not illustrated). Again, the pupillary image or iris image can be used with eye tracking techniques to determine the relative position of eye 270 to retinal imaging system 200 during a preview phase. In other words, the pupillary image or iris image can be analyzed and correlated to the direction and magnitude of a lateral misalignment. In one embodiment, the initial image may be acquired using IR illumination, so as not to elicit an iris contraction during the previous phase prior to acquiring the regular retinal images. In other embodiments, other chromatic or broad-spectrum flash illumination may be used.

After the magnitude of a lateral misalignment has been determined, that lateral misalignment is compared against a threshold misalignment value (decision block 920). In one embodiment, the threshold misalignment magnitude is selected to be 1 mm; however, other threshold misalignment values either greater or smaller may be selected. In one embodiment, the threshold misalignment value may be selected to be any value greater than zero. If the determined lateral misalignment is determined to be less than the threshold misalignment value (decision block 920), then process 900 continues to process block 935 where the subsequent retinal image (or burst of retinal images) are acquired with image sensor 210.

However, if the determined lateral misalignment is determined to be greater than the threshold misalignment (decision block 920), then process 900 continues to a process block 925 where a visual position of the dynamic fixation target is adjusted (e.g., repositioned on display 225, physically moving display 225, intervening optics used to change a perceived position, etc.). In process block 925, the direction of the repositioning and the magnitude of the repositioning of the dynamic fixation target is based upon and correlated to the direction of the lateral misalignment and the magnitude of the lateral misalignment calculated in process 915. In one embodiment, a lookup table may be used to correlate the analyzed characteristics of the initial eye image to direction and magnitude of adjustments to the position of the dynamic fixation target on display 225.

As discussed above, the dynamic fixation target provides a visual cue to eye 270 upon which the patient can fixate. As such, a repositioning of the dynamic fixation target while otherwise holding retinal imaging system 200 steady relative to the patient's head, encourages eye 270 to rotate. By selecting the amount and direction of this repositioning, dynamic fixation target encourages eye 270 to roll towards the direction of lateral offset to compensate for the lateral misalignment. Furthermore, this repositioning of the dynamic fixation target may also be motivated to move one or more image artifacts 105 to different positions. The repositioning may be executed during a pre-view phase to obtain a desired alignment, at which point one or more retinal images are acquired in process block 935. Alternatively, the repositioning may be executed between successive retinal images or between bursts of retinal images for image stacking. The determination of threshold alignment or threshold misalignment includes alignments that advantageously reposition image artifacts 105 to achieve artifact free images of certain portions (or all portions) of the retina.

The dynamic fixation target may be repositioned to a new temporary fixed location or continuously repositioned in a pattern (decision block 930). In the embodiment where the dynamic fixation target is repositioned to a new temporary fixed location, process 900 continues to a process block 935 where the retinal image is acquired by image sensor 210. Accordingly, the retinal image is acquired while the eye is encouraged to rotate, after the eye has been encouraged to rotate, or as the eye is encouraged to rotate. In a decision block 940, the retinal image may be analyzed to determine whether its quality is acceptable (or whether a given image artifact was sufficiently moved away from a certain position), and if so, it is stored (process block 945). If the retinal image includes unacceptable defects (e.g., greater than threshold lateral misalignment still present) or if one or more image artifacts still need to be repositioned to achieve sufficient imaging coverage of the retina, then process 900 loops back to process 910 and repeats. In embodiments that analyze the retinal image in process block 915 to determine alignment, process 900 may alternatively loop back to process block 915 and reanalyze the retinal image acquired in process block 935 for readjustments to the position of the dynamic fixation target. Storing of the retinal image(s) in process block 945 may include combining or stacking multiple retinal images into a single composite retinal image that is free of image artifacts or at least sufficiently free of image artifacts in the region or regions of interest.

Returning to decision block 930, in place of repositioning the dynamic fixation target to temporary fixed locations, the dynamic fixation target may be continuously moved in a repeating pattern (e.g., a circle, oval, back-and-forth jitter, etc.) that encourages the eye to sweep through the direction that compensates for the lateral misalignment (process block 950). Image acquisition may be synchronized with the sweeping motion of eye 270 and acquired in process block 935. In one embodiment, image sensor 210 acquires a burst of retinal images during the illumination flash time as eye 270 sweeps through the gaze direction that compensates for the lateral misalignment. The burst images can then be analyzed to identify which image has the best image quality (i.e., acquired at the optimal compensating position).

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A retinal imaging system, comprising:
   an eyepiece lens assembly;
   an image sensor adapted to acquire a retinal image of an eye through the eyepiece lens assembly;
   a dynamic fixation target optically coupled to the eyepiece lens assembly such that the dynamic fixation target is viewable through the eyepiece lens assembly; and
   a controller communicatively coupled to the image sensor and the dynamic fixation target, the controller including logic that when executed by the controller causes the retinal imaging system to perform operations including:
      acquiring a first image of the eye;
      analyzing the first image to determine if a misalignment is present between the eye and the eyepiece lens;
      in response to determining the misalignment is present, adjusting a visual position of the dynamic fixation target to encourage a user to move the eye in a direction that compensates for the misalignment; and
      acquiring the retinal image of the eye after adjusting the visual position of the dynamic fixation target.

2. The retinal imaging system of claim 1, wherein the retinal image comprises a second retinal image and wherein the first image of the eye comprises a first retinal image acquired with the image sensor.

3. The retinal imaging system of claim 2, wherein analyzing the first image to determine if the misalignment is present comprises:
   comparing image qualities between different regions of the first retinal image.

4. The retinal imaging system of claim 2, wherein analyzing the first image to determine if the misalignment is present comprises:
   analyzing the first retinal image for a presence of one or more corneal reflections; and
   correlating the one or more corneal reflections to a lateral decentered position of the eye relative to the eyepiece lens assembly.

5. The retinal imaging system of claim 1, further comprising:
   an alignment tracking camera communicatively coupled to the controller and disposed to capture images of a pupil or an iris of the eye, and wherein the first image of the eye comprises a pupillary image or an iris image.

6. The retinal imaging system of claim 5, wherein analyzing the first image to determine if the misalignment is present comprises:
   correlating the pupillary image or the iris image to a lateral decentered position of the eye relative to the eyepiece lens assembly.

7. The retinal imaging system of claim 1, further comprising:
   an illuminator communicatively coupled to the controller and positioned to illuminate the eye with infrared (IR)

light while acquiring the first image, wherein the first image comprises an IR image of the eye to reduce iris contraction prior to acquiring the retinal image.

8. The retinal imaging system of claim 1, wherein adjusting the visual position of the dynamic fixation target comprises:
adjusting the visual position of the dynamic fixation target to encourage the eye to rotate towards the direction of the misalignment; and
adjusting the visual position of the dynamic fixation target by an amount correlated to a magnitude of the misalignment.

9. The retinal imaging system of claim 1, wherein the dynamic fixation target comprises a virtual fixation target generated by a display optically coupled with the eyepiece lens assembly to display the virtual fixation target through the eyepiece lens assembly.

10. The retinal imaging system of claim 1, wherein adjusting the visual position of the dynamic fixation target comprises:
continuously adjusting the visual position of the dynamic fixation target in a repeating pattern that encourages the eye to sweep through the direction that compensates for the misalignment; and
synchronizing the acquiring of the retinal image with the continuously adjusting of the visual position of the dynamic fixation target to acquire the retinal image when the eye is moved to compensate for the misalignment.

11. A method of imaging a retina with a retinal imaging system, the method comprising:
displaying a dynamic fixation target at an initial visual position;
acquiring a first image of an eye with the dynamic fixation target at the initial visual position;
analyzing the first image to determine whether a misalignment, that is greater than a threshold misalignment, is present between the eye and an eyepiece lens assembly of the retinal imaging system;
in response to determining the misalignment is present, adjusting the dynamic fixation target to a revised visual position that encourages the eye to move in a direction that compensates for the misalignment; and
acquiring a second image of the eye while the dynamic fixation target is at the revised visual position, wherein the second image comprises a retinal image.

12. The method of claim 11, wherein the retinal image comprises a second retinal image and the first image of the eye comprises a first retinal image acquired with a retinal image sensor imaging through the eyepiece lens assembly.

13. The method of claim 12, wherein analyzing the first image to determine whether the misalignment is present comprises:
comparing image qualities between different regions of the first retinal image.

14. The method of claim 12, wherein analyzing the first image to determine whether the misalignment is present comprises:
analyzing the first retinal image for a presence of one or more corneal reflections; and
correlating the one or more corneal reflections to a lateral decentered position of the eye relative to the eyepiece lens assembly.

15. The method of claim 11, wherein the first image of the eye comprises a pupillary image or an iris image captured with a eye tracking camera that is separate and distinct from a retinal image sensor used to capture the retinal image.

16. The method of claim 15, wherein analyzing the first image to determine whether the misalignment is present comprises:
correlating the pupillary image or the iris image to a lateral decentered position of the eye relative to the eyepiece lens assembly.

17. The method of claim 11, further comprising:
illuminating the eye with infrared (IR) light while capturing the first image as an IR image of the eye to reduce iris contraction prior to acquiring the second image.

18. The method of claim 11, wherein adjusting the dynamic fixation target to the revised visual position that encourages the eye to move in the direction that compensates for the misalignment comprises:
adjusting the dynamic fixation target to encourage the eye to move towards the direction of the misalignment; and
adjusting the dynamic fixation target by an amount correlated to a magnitude of the misalignment.

19. The method of claim 11, wherein displaying the dynamic fixation target comprises generating a virtual fixation target with a display optically coupled with the eyepiece lens assembly to output the virtual fixation target through the eyepiece lens assembly.

20. The method of claim 11, wherein adjusting the dynamic fixation target to the revised visual position that encourages the eye to move in the direction that compensates for the misalignment comprises:
continuously moving the dynamic fixation target in a repeating pattern that encourages the eye to sweep through the direction that compensates for the misalignment.

* * * * *